(12) United States Patent
Hildebrand et al.

(10) Patent No.: US 6,287,764 B1
(45) Date of Patent: *Sep. 11, 2001

(54) CLASS I SEQUENCE BASED TYPING OF HLA-A, -B, AND -C ALLELES BY DIRECT DNA SEQUENCING

(76) Inventors: William H. Hildebrand, 900 Northcreek Dr., Edmond, OK (US) 73034; Mary Ellexson, 803 E. Drive, Apt. B, Oklahoma City, OK (US) 73105; Pierre Chretien, 7793 Rue de Gaspe, Montreal, Quebec (CA), H2R2A5; R. Scott Duthie, 2767 S. Linebarger Terr., Milwaukee, WI (US) 53207

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 10 days.

(21) Appl. No.: 09/021,892
(22) Filed: Feb. 11, 1998

Related U.S. Application Data
(60) Provisional application No. 60/037,054, filed on Feb. 11, 1997.

(51) Int. Cl.[7] .............................. C12Q 1/68; C12P 19/34; C12N 15/12
(52) U.S. Cl. ........................ 435/6; 435/91.2; 536/23.5; 536/24.33; 536/25.32
(58) Field of Search ............................. 435/6, 91.1, 91.2; 536/24.33, 25.3, 25.32, 23.5

(56) References Cited

U.S. PATENT DOCUMENTS 5,424,184 * 6/1995 Santamaria et al. ..................... 435/6
5,451,512    9/1995  Apple, et al. .
5,512,439    4/1996  Hornes, et al. .
5,593,830    1/1997  Santamaria, et al. .
5,618,701 *  4/1997  Landegren ........................ 435/91.1

OTHER PUBLICATIONS

Gibco BRL catalog Life Technologies Inc. Gaithersburg, MD pp.762–763, 1992.*

Oetting et al. Linkage analysis with multiplexed short tandem repeat polymorphisms using infrared fluorescence and M13 tailed primers. Genomics vol. 30 pp. 450–458, 1995.*

Cereb et al. Locus–specific amplification of HLA class I genes from genomic DNA: locus–spefic sequences in the first and third introns of HLA–A, –B, and –C alleles. Tissue Antigens vol. 45 pp. 1–11, 1995.*

Domena et al. A Small Test of a Sequence–Based Typing Method: Definition of the B*1520 Allele, pp. 217–224, 1994.

* cited by examiner

*Primary Examiner*—John S. Brusca
(74) *Attorney, Agent, or Firm*—Dunlap, Codding & Rogers, P.C.

(57) ABSTRACT

There is provided a method for directly typing or sequencing HLA-A, -B, or -C alleles from a tissue sample wherein exons 2 and 3 of the HLA-A, -B, or -C alleles from the sample are amplified together in a locus specific manner and then separated out and individually amplified in a locus specific manner. After the two amplifications, the amplified exons are directly sequenced, the sequences are recombined, and a comparison is made between the derived HLA allele sequence and an HLA allele database, thereby giving an exact HLA-A, -B, or -C type for the sample being tested.

4 Claims, 3 Drawing Sheets

CLASS I SEQUENCE BASED TYPING OF HLA-A, -B, AND -C ALLELES BY DIRECT DNA SEQUENCING

CROSS REFERENCE TO RELATED APPLICATIONS

This application claims the benefit of U.S. Provisional Application Ser. No. 60/037,054, filed Feb. 11, 1997.

FEDERALLY SPONSORED RESEARCH OR DEVELOPMENT

This invention was developed through assistance with the National Marrow Donor Program (NMDP, contract number 7105) and the Department of Defense, Office of Naval Research (grant number N00014-95-9974).

BACKGROUND OF THE INVENTION

1. Field of the Invention

The present invention relates in general to a method for direct DNA sequencing of HLA-A, -B, and -C alleles and more particularly the invention entails the sequence based typing of exons 2 and 3 for the HLA allele gene under study.

2. Brief Description of the Related Art

MHC has the highest genetic polymorphism of the mammalian DNA molecules. Questions are raised by this polymorphism, such as its molecular basis, degree, and functional significance. For analysis of MHC polymorphism and its relationship to immune responses and disease susceptibilities, the human species has considerable scientific advantages, as well as direct relevance to clinical medicine. Only in human populations is there likely to be extensive analysis of MHC polymorphism from many geographically separated populations. The crystal structure of the human class I molecule has also been previously disclosed, making accurate insights into other HLA class I molecules possible as well as the allelic polymorphism of the HLA-A, B and C genes.

The HLA class I genes are a component of the human major histocompatibility complex (MHC). The class I genes consist of the three classical genes encoding the major transplantation antigens HLA-A, HLA-B and HLA-C and seven non-classical class I genes, HLA-E, HLA-F, HLA-G, HLA-H, HLA-J, HLA-K, and HLA-L.

The classical HLA class I genes encode polymorphic cell surface proteins expressed on most nucleated cells. The natural function of these proteins is to bind and present diverse sets of peptide fragments from intracellularly processed antigens to the T cell antigen receptors (TCRs). Thus, the peptide-binding capacity of the MHC molecule facilitates immune recognition of intracellular pathogens and altered self proteins. Therefore, by increasing the peptide repertoire for TCRs, the polymorphism of MHC molecules plays a critical role in the immune response potential of a host. On the other hand, MHC polymorphism exerts an immunological burden on the host transplanted with allogeneic tissues. As a result, mismatches in HLA class I molecules are one of the main causes of allograft rejection and graft versus host disease, and the level of HLA matching between tissue donor and recipient is a major factor in the success of allogeneic tissue and marrow transplants. It is therefore a matter of considerable medical significance to be able to determine the "type" of the HLA class I genes of candidate organ donors and recipients.

HLA class I histocompatibility antigens for patient-donor matching are conventionally determined by serological typing. Biochemical and molecular techniques have revealed that HLA class I polymorphism is far greater than previously recognized by conventional methods. To date, over 59 HLA-A, 127 HLA-B, and 36 HLA-C different allelic sequences have been identified. This high level of allelic diversity complicates the typing of the HLA class I genes.

Another complicating factor is the large number of homologous genes and alleles. Each of the HLA class I genes is composed of eight exons and seven introns and the sequences of these exons and introns are highly conserved across the HLA class I genes. Allelic variations mostly occur in exons 2 and 3 which are flanked by noncoding introns 1, 2, and 3. These two exons encode the functional domains of the molecules.

Taken together, these two complications make HLA class I typing at the nucleic acid level a formidable task. Allelic diversity within any one gene means that a great many probes need to be developed if hybridization-based tests are used in the typing. Further, the general applicability of DNA typing methods to HLA class I genes depends on the design of primers which provide effective locus-specific amplification of exons 2 and/or 3 of one HLA class I gene.

One method for performing HLA class I typing is disclosed in U.S. Pat. No. 5,424,184 which is incorporated herein by reference. This patent utilizes primers which are located within exons 2 and 3 of the HLA class I genes to achieve what is described as group-specific amplification of a portion of the HLA-A, HLA-B, and HLA-C genes. This approach is not ideal, however, since the primers hybridize with portions of the coding strand, and thus may mask significant allelic variations. In addition, this method requires a grouping of alleles by means of another method in order to select group-specific primers for amplification.

Prior to inclusion of polymerase chain reaction (PCR) into the cloning and sequencing of HLA class I alleles the accumulation of class I sequences was a cumbersome act. The advent of the PCR greatly accelerated the accumulation of class I HLA sequences. Since then, research has been undertaken to bring molecularly-based HLA class I and class II typing techniques to the point where they would be clinically useful and cost-beneficial for the many applications such as bone marrow donor registry and disease association studies.

Using the bone marrow donor registry as an example, the impetuses driving the development of new semi-automated and automated molecular techniques for high-resolution class I and class II typing could be characterized as: (1) the pool of available donors in the registry were poorly HLA typed: many HLA class I types are of low resolution and many clinically deleterious class I types were missed; (2) questions pertaining to discriminatory power of serology had to be addressed: serological HLA typing does not correlate with a high degree of accuracy with the molecular typing of HLA alleles; (3) it is recognized that continual HLA typing will be required to establish and maintain a donor registry of sufficient size; and (4) typing methods based on DNA sequence have many advantages over conventional serologic typing techniques including the elimination of typing complications due to different tissue distributions of MHC antigens, the use of defined reagents available in unlimited quantities (in contrast to alloantisera which are chemically ill-defined, limited in amount, and frequently monopolized), and the ability to provide an absolute HLA type.

For HLA class II molecules, high resolution clinical typing using the polymerase chain reaction (PCR) with sequence specific primers (SSP) and/or sequence specific oligonucleotide probes (SSOP) is now a routine procedure. This advance in class II typing was essential because alloantisera, traditionally used for class I typing, proved especially inadequate for typing class II antigens. An additional advantage of DNA based HLA typing is that viable cells are not required.

An increasing appreciation of the complexity and the extent of HLA class I polymorphism has consequently developed. The shortcomings of current class I serological typing procedures became more apparent, as did the need for a high resolution molecular typing technique. As a logical extension of methods successfully employed for class II typing several groups have applied PCR/SSP and/or PCR/SSOP methodologies to molecularly type HLA class I alleles. At first these applications were most successful for the subtyping of class I antigens for which there are multiple variants (e.g. A2, B27). These techniques subsequently began to prosper for the typing of all alleles at the HLA-A, and C loci, with the HLA-B locus providing the most resistance to these typing methodologies.

The nucleic acid sequencing of class I HLA molecules has revealed numerous serological typing inadequacies, and the availability of cell lines containing sequenced class I alleles has been instrumental for the development of PCR primer and probe based typing techniques. Well characterized cell lines serve as important developmental standards and controls for these arriving class I molecular typing techniques. It is anticipated that this will hold true for emerging HLA-B typing protocols.

Attempts to eliminate cloning from the determination of HLA class I sequences has been undertaken. To obviate cloning for direct sequence based class I typing three difficulties arise. The first difficulty is that sequence based typing must frequently resolve two nucleotides at one rung of the sequencing ladder; heterozygosity is the norm, and two alleles at one locus may differ by as many as 85 nucleotides. We therefore sought a DNA sequencer designed to utilize a single fluorophore, eliminating complications which might arise from different fluorophores simultaneously fluorescing in the same lane at heterozygous positions. The second difficulty is the occurrence of band compressions in the sequencing ladder due to the high G/C content of class I molecules. Past experience dictates that optimal resolution of G/C band compressions is obtained with a T7 sequencing chemistry utilizing 7-deaza dGTP. A third difficulty encountered by all who type class I HLA molecules is their polymorphic nature; once the class I DNA sequence is obtained, it is often difficult to assign a class I type to the data generated.

The problem addressed is that for the successful transplantation of organs and bone marrow, for the proper diagnosis of autoimmune disorders such as arthritis, and for research studies trying to establish a link between a particular disease and immune response genes, an accurate class I HLA type must be established. However, clinical HLA class I typing laboratories (which now use antibodies for typing) cannot accurately discriminate among the many different class I genes found in the population. Therefore, molecular DNA based methods are being tested to facilitate more precise HLA class I typing.

Others are testing molecular DNA class I HLA typing methodologies. Some rely on the failure or ability to PCR amplify a gene, with several hundred PCR reactions needed to call a class I type. This is termed SSP (sequence specific PCR). Other techniques utilize one HLA-A, -B, and -C locus specific PCR reaction followed by hybridization with a complex series of oligonucleotide probes. This technique is referred to as SSOP. These techniques utilize a similar first step—an HLA-A, -B, and -C locus specific PCR reaction—followed by divergent methods for typing the HLA-A, -B, or -C specific PCR product.

A comparison of SSP, SSOP, and the present invention which we will term "sequence based typing" (SBT) shows that SBT gives a precise class I HLA type, while SSP and SSOP give only a partial type, i.e. they probe portions of the genes being typed while SBT reads all of the gene being typed. The reason others have been reluctant to adopt a sequence based typing approach is because the technology is complex and developing.

Due to the fact that SBT gives the most precise class I type, several other groups have tried to develop a class I HLA SBT method. What individuates the techniques described herein is: (1) amplification of HLA-A, -B, or -C class I alleles such that exons 2 and 3 are produced in a locus specific way to facilitate (2) production of a secondary HLA-A, -B, or -C locus specific polymerase chain reaction by separately amplifying exons 2 and 3 using the primary polymerase chain reaction product as a template and nested or heminested polymerase chain reaction primers and (3) preparing the secondary polymerase chain reaction product such that it has an anchoring moiety at one terminus and a DNA sequencing primer site at the opposing terminus and (4) following attachment to a solid support the secondary polymerase chain reaction products are then DNA sequenced.

Thus, the novel aspect of our approach is that HLA-A, -B, or -C locus specific nested polymerase chain reaction products are produced at a level of purity sufficient for DNA sequence based typing. Furthermore, these secondary polymerase chain reaction products can be anchored to a solid support prior to DNA sequencing with a universal DNA sequencing primer.

SUMMARY OF THE INVENTION

We have developed a method for typing HLA class I alleles in order to determine the HLA-A, -B, or -C type of a sample. Our method comprises two amplification steps to amplify, purify, and separate exons 2 and 3 in a locus specific manner. In particular, the method comprises the steps of: (a) amplifying HLA-A, -B, or -C alleles so as to provide a primary amplicon, wherein the primary amplicon comprises amplified exons 2 and 3 of the HLA-A, -B, or -C alleles in a locus specific manner; (b) producing at least two secondary HLA-A, -B, or -C locus specific amplicons corresponding to each of the exons 2 and 3 of the primary amplicon, wherein the at least two secondary amplicons are produced by amplifying the primary amplicon by means of using the primary amplicon as a template and nested polymerase chain reaction primers, thereby independently framing each of exon 2 and exon 3; (c) preparing the at least two secondary amplicons for sequencing, wherein the at least two secondary amplicons are provided with an anchoring moiety attached to a first terminus of each of the at least two secondary amplicons and a sequencing primer site attached to a second terminus of each of the at least two secondary amplicons; (d) attaching the anchoring moiety of each of the at least two secondary amplicons to solid supports; and (d) DNA sequencing each of the at least two secondary amplicons.

In a preferred embodiment, the method further comprises the step of analyzing the DNA sequence of the at least two secondary amplicons so as to provide an HLA class I type for the at least two secondary amplicons. It is also contemplated that in the step of preparing the at least two secondary amplicons, the anchoring moiety comprises a biotin molecule and that the DNA sequencing primer comprises a M13 universal primer, such as primer GTA AAA CGA CGG CCA SEQ ID NO.1.

The invention also comprises a method for determining tissue compatibility. In particular this method is comprised of the steps of: (a) obtaining a sample of tissue, wherein the sample of tissue contains an amount of DNA encoding the HLA-A, -B, or -C alleles; (b) amplifying the HLA-A, -B, or -C alleles so as to provide a primary amplicon, wherein the primary amplicon comprises amplified exons 2 and 3 of the HLA-A, -B, or -C alleles in a locus specific manner; (c) producing at least two secondary HLA-A, -B, or -C locus specific amplicons corresponding to each of the exons 2 and 3 of the primary amplicons, wherein the at least two secondary amplicons are produced by amplifying the primary amplicon by means of using the primary amplicon as a template and nested polymerase chain reaction primers located in introns 1, 2, and 3, thereby independently framing each of exon 2 and exon 3; (d) preparing the at least two secondary amplicons for sequencing, wherein the at least two secondary amplicons are provided with an anchoring moiety attached to a first terminus of each of the at least two secondary amplicons and a sequencing primer site attached to a second terminus of each of the at least two secondary amplicons; (e) attaching the anchoring moiety of each of the at least two secondary amplicons to solid supports; (f) DNA sequencing each of the at least two secondary amplicons; and (g) comparing the DNA sequence of the at least two secondary amplicons with at least one predetermined tissue sample.

DETAILED DESCRIPTION OF THE INVENTION

Figure 1:
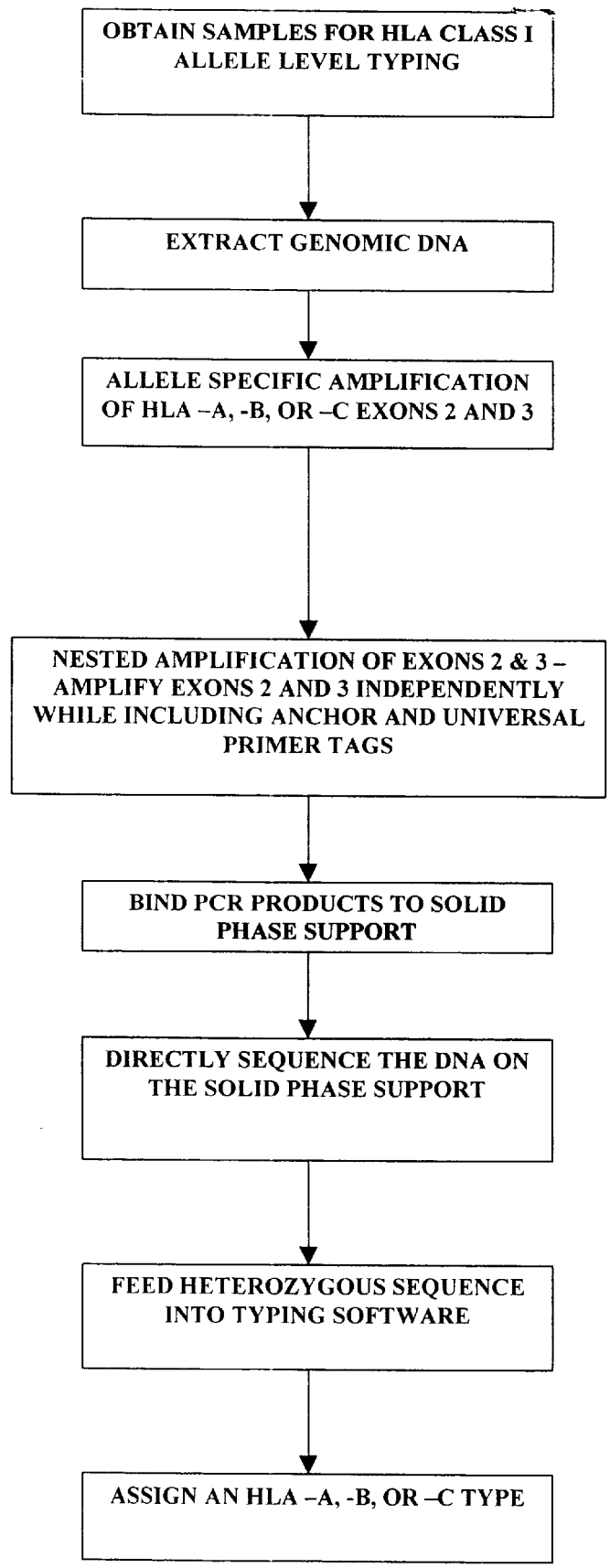
FIG. 1 is a flow diagram showing in particular the steps for determining a class I HLA sequence-based type with the direct DNA sequence analysis of the present invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2:
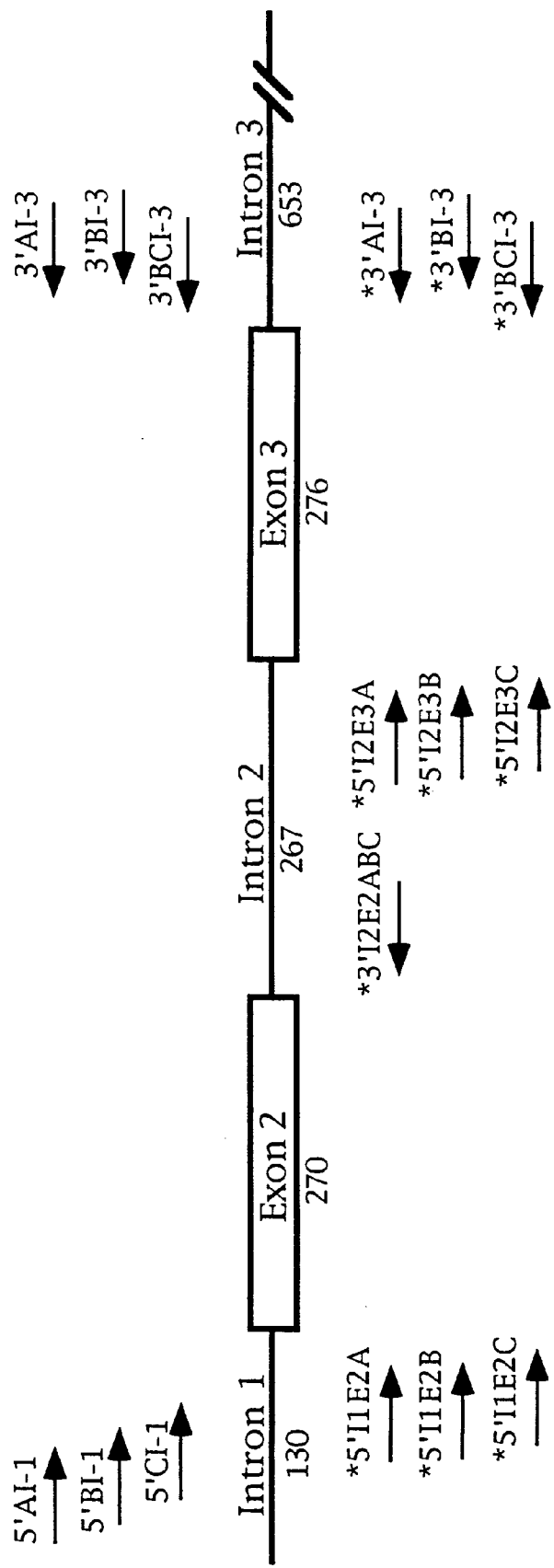
FIG. 2 is a diagram indicating the primers and introns/exons used in determining a class I HLA sequence-based type with direct DNA sequence analysis, showing in particular the primers listed in Table 1 and their relative positioning during the amplification steps.
Figure 3:
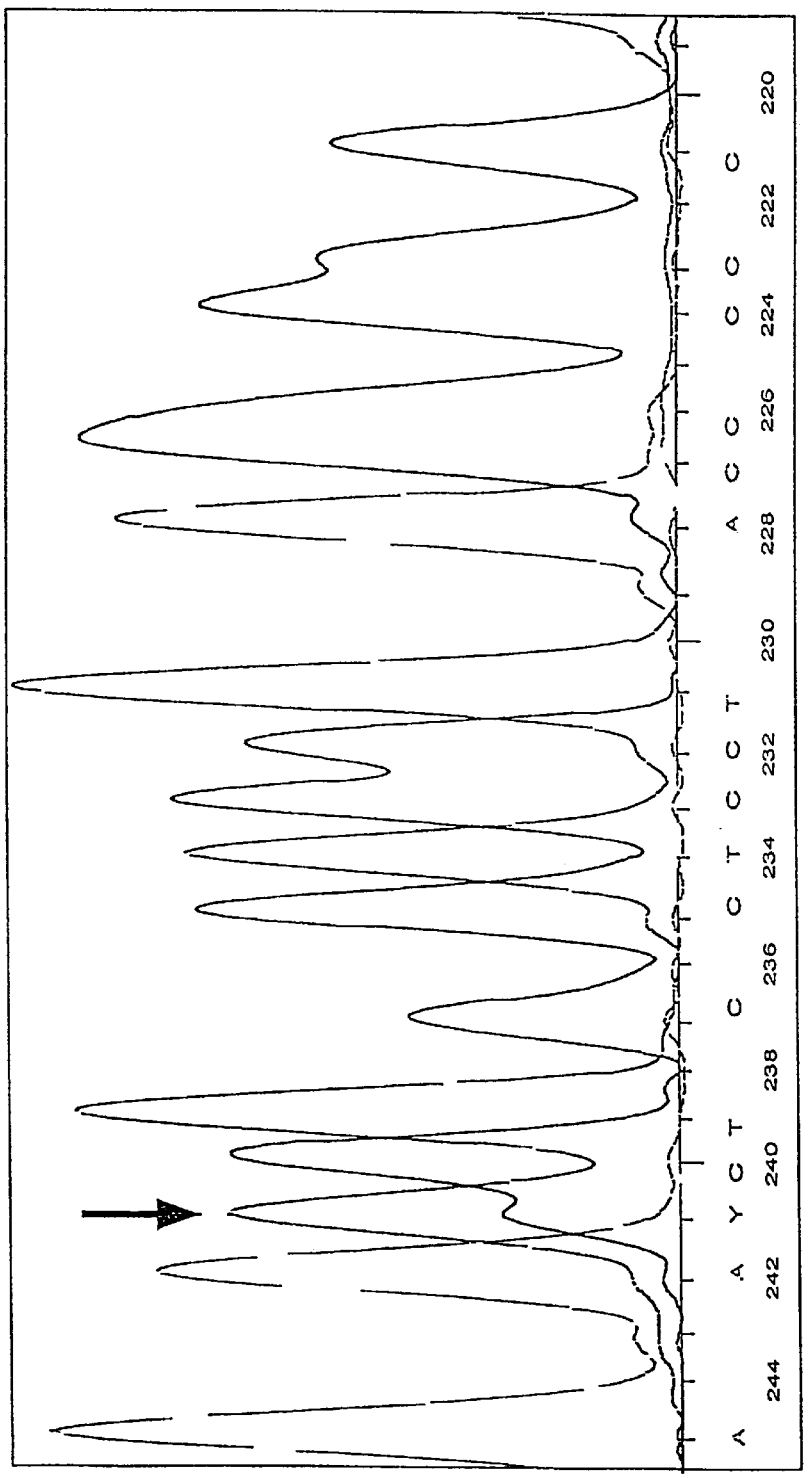
FIG. 3 is a chromatogram showing a heterozygous position (arrow) on a Pharmacia ALF automated DNA sequencer in accordance with the method for determining a class I HLA sequence-based type with direct DNA sequence analysis of the present invention.

The invention encompasses a method for determining HLA type via HLA-A, -B, -C locus specific amplification of exons 2 and 3 (as shown diagrammatically in FIG. 1). In particular, the method includes performing two nested PCR's on exon 2 and two hemi-nested PCR's on exon 3. The purpose of these nested PCR reactions is to generate PCR products which are approximately 350 nucleotides in length and to produce PCR products containing anchoring moieties for binding to a solid phase medium such as a Streptavidin coated support, wherein the Streptavidin coated support may be a comb or bead or any other structure capable of binding the PCR product. For sequence based typing of HLA class I alleles the claimed invention utilizes two DNA sequencing reactions per exon, with the sequencing primers built onto the PCR primer which opposes the biotinylated primer so that universal sequencing primers flank the exons being sequenced (FIG. 2). In this way, bidirectional sequences throughout exons 2 and 3 can be obtained. Read lengths in which class I HLA heterozygous positions are resolved generally range from 300–350 nucleotides from either direction, with heterozygous positions proximal to the sequencing primers best resolved. Following this scheme, positions of heterozygosity immediately adjacent to each primer are most clearly resolved, while it becomes more difficult to resolve heterozygous positions as reads progress beyond 350 bases from each sequencing primer. Before determining a class I type the invention requires that the positions of heterozygosity be clearly resolved beyond 200 nucleotides for both sequencing reads in each exon.

Once it is clear that heterozygous positions 200 or more nucleotides from each primer can be resolved, the two sequencing reads at each exon are assembled and then combined with the assembled sequence from the other exon for that sample. It is at the assembly of the two sequencing reads for each exon that the typing software is required. With a software package capable of assembling the exon 2 and the exon 3 DNA sequences, opposing reads for each exon are automatically reversed complemented, aligned, and linked together, after which the software combines the sequence of exons 2 and 3 for each sample. The software then compares all possible combinations of HLA-A, -B, or -C alleles in an existing HLA class I database to the assembled sequencing data. The software then sequentially ranks the pairs of HLA class I alleles which best fit the sequence data and lists the number of positions not consistent with the best fit pair of alleles in the class I database.

The software is arranged so that ambiguities and questioned calls are flagged, and flagged calls are readily viewed in the chromatograms which are present in the software window. The technique described herein is not foolproof in that <1% of the HLA-A and HLA-B heterozygous combinations of alleles are non-unique through exons 2 and 3 and cannot be resolved with this SBT technique. For example, the current method cannot distinguish a B*1501/B*4008 DNA sequence combination from a B*1508/B*4002 individual, such that a second class I HLA typing step (i.e. PCR-SSP) or a third sequencing reaction through exons 4–8 will sometimes be required. However, this is true of any technique that types only exons 2 and 3. One of ordinary skill in the art would appreciate that the level of resolution obtained is beyond that of other methodologies.

In the present invention, primers utilized in the primary PCR are different to previously published HLA locus-specific amplification primers Cereb et al., *Tissue Antigens* 47:498–511 (1996). However, most important is that the PCR product generated in the primary PCR is not directly evaluated to determine an HLA type. Rather it is used as an intermediate template for a secondary nested PCR which amplifies exons 2 and 3 separately. In the secondary PCR either the 5' or 3' primer is labeled with a generic, M13 universal, primer site to facilitate annealing of a DNA sequencing primer and the opposing 5' or 3' primer is labeled with an anchor, biotin, to promote solid phase DNA sequencing. Also of significance is that one of the two nested secondary PCR primers used to amplify each exon contains locus specificity to avoid evaluation of undesired amplicons obtained in the primary PCR. Those nested PCR primers are located in the introns flanking exons 2 and 3. This technique therefore requires two rounds of locus-specific amplification prior to HLA class I evaluation. The secondary PCR product is then evaluated to determine an allelic HLA class I type.

The inventor is aware that these primers may be modified by introducing degenerate bases where alternative bases may occur as new alleles are detected. These primers may also be made somewhat longer or shorter. Other modifications may include the introduction of various generic sequencing primer sites other than the M13 universal sequencing primer site used here and the use of alternative moieties other than Biotin for the adherence of the sequencing product to a solid-phase medium such as, but not limited to, combs, magnetic beads, or plates which are coated with a complementary substance possessing an affinity for the generated sequencing product.

EXAMPLE I

Once a sample is obtained, the first step is to treat the tissue sample so as to obtain nucleic acids for amplification. The method herein described can be performed on whole blood, tumor cells, sperm, hair follicles, or any other nucleated tissue sample.

A. Locus Specific Amplification of HLA-A, -B, -C Alleles and of Exons 2 and 3

Genomic DNA was extracted from 200 µL of whole blood using the Qiagen DNA extraction kit otherwise known as a "QIAamp blood kit" according to the supplied protocol. Exons 2 and 3 of HLA class I-A, -B, and -C loci were PCR amplified from 500 ng of genomic DNA using 20 picomoles of HLA class I locus specific primers located within introns 1 and 3 (Table 1).

The primers listed in Table 1 correspond to the bases which are the same across the introns and are indicated as a single base (A, C, G, T), while bases which are variable across the introns are indicated by a code for alternative bases. In general, it will be advantageous to select the primer that will avoid the variable bases.

Specific buffers and reagents used for this PCR have been previously described in the literature and one of ordinary skill in the art would appreciate that any PCR buffer is contemplated for use provided that it functions to amplify exons 2 and 3.

Once the sample has been treated, it is combined with two amplification primers and amplified, for example using PCR amplification. The basic process of PCR amplification is known, for example from U.S. Pat. Nos. 4,683,202 and 4,683,195, which are incorporated herein by reference. In PCR amplification, two amplification primers are used, each of which hybridizes to a different one of the two strands of a DNA duplex. Multiple cycles of primer extension, and denaturation are used to produce additional copies of DNA extending from the position of one primer to the position of the other. In this way, the number of copies of the genetic material positioned between the two primer binding sites is increased.

In the present invention, amplification of exons 2 and 3 is preferably performed using at least one locus-specific primer which specifically hybridizes to a portion of intron 1 or intron 3. As used in the specification and claims hereof, the primers which "specifically hybridize" to the introns are primers which permit locus-specific amplification by having a sequence which is exactly complementary to the expected sequence of a portion of the intron so that binding and amplification can occur, but which is not complementary to a region on any of the other HLA class I genes. It will be understood that locus-specific primers within the scope of this invention need not be complementary to a totally unique sequence within the human genome, provided that both members of the primer pair used in amplification do not bind to the same gene outside the gene of interest.

Amplification primers useful in the present invention are generally from 10 to 40 bases in length, more preferably from 17 to 35 bases in length. Within this size range, we have identified suitable locus-specific, group-specific and allele-specific primers for each of the classical HLA class I genes.

Degenerate bases can be introduced in the primer sequences where alternative bases occur among alleles. These primers are complementary to the region of the non-coding strand spanning nucleotides 26–46 and 21–45, respectively of the intron 1 sequence shown in FIG. 2 (Seq. ID No.:1). It will be appreciated that this primer could be made longer by adding additional complementary bases to the 5'-end. The primer might also be made somewhat shorter, for example spanning nucleotides 26–44, since nucleotides 23, 24, and 25 are identical across the various HLA-locuses in sequences of which the inventors are aware. In addition to primers binding to the non-coding strand, it will be appreciated that complementary primers which bind to the corresponding portions of the coding strand could be used with a compatible second primer. The use of longer or shorter locus-specific primers, and of complementary locus-specific primers are within the scope of the present invention.

While PCR amplification is the preferred approach to amplification of the treated sample, other techniques which use oligonucleotide primers to define a region of DNA to be amplified can be used as well. Such techniques include ligase chain reaction amplification (Wiedmann et al., PCR Primer, Laboratory Manual, Cold Spring Harbor (1991)).

The first amplification procedure results in the production of an amplified product, in which the region of the HLA-A, -B, or -C gene between the two primers is significantly increased in concentration relative to other genetic material in the treated sample.

The first PCR amplification was accomplished on a thermocycler programmed for an initial denaturation cycle of 96°, 2:00; then 39 cycles of 94°, 0:30; 56°, 0:50 +1 s/cycle; 72°, 0:30 +2 s/cycle. Individual exons obtained from the first locus specific PCR amplification were then amplified a second time individually by (5 µL of a 1:200 dilution) using 10 picomoles of HLA class I locus and exon specific primers listed in Table 1. Reagents contained within this 60 µL PCR were as follows: 10 mM Tris-HCl, (pH 8.3) 50 mM KCl, 1.5 mM MgCl$_2$, 0.001 (w/v) gelatin, 0.2 mM dNTPs and 2.5 U of Taq DNA polymerase. Cycling conditions for this PCR were 30 cycles of 95°, 1:00; 54°, 1:00; 72°, 1:00.

B. Direct DNA Sequencing Approach

Once exons 2 and 3 have been amplified a first time together and a second time separately, they may be sequenced directly and as generally described in Santamaria et al., Hum. Immunology 37:39–50 (1993). The twice amplified product can be sequenced using the well-known dideoxy chain termination method. Briefly, in this method a sequencing primer complementary to one strand of the amplified product is combined with the amplified product, a template-dependent polymerase enzyme, a mixture of the four standard nucleotide bases (A, G, T, and C) and one type of dideoxy nucleotide base. The bases are added to the end of the amplification primer to form a new oligonucleotide complementary to the amplification product. When a dideoxy base is added, however, no additional bases can be added. This results in the formations of a family of oligonucleotides whose lengths reflect the positions of the nucleotide base provided in dideoxy form within the complementary oligonucleotide. By evaluating the fragments formed in four reactions mixtures, one for each type of dideoxy nucleotide base, by gel electrophoresis, the sequence of the complementary strand can be deduced.

Basic procedures for performing nucleic acid sequencing in this manner are well known in the art, and commercial instruments are available for this purpose. Thus, sequencing is a routine procedure provided that amplified DNA and suitable primers are available. In this case, the same primers used to amplify the DNA can be used as sequencing primers.

Nested intron primers can also be used as sequencing primers. These primers are complementary to the sequences of the amplified products located in intron 1, intron 2, or intron 3 (SEQ ID Nos.:1–9). It is particularly advantageous to have "universal" sequencing primers which could be used in the sequencing of any of the major transplantation antigen genes after locus-specific amplification, and such primers are an aspect of the present invention, such as universal primer M13.

Use of the AutoLoad Solid Phase Sequencing Kit from Amersham Pharmacia Biotech was used for this portion of the DNA sequencing, however, one of ordinary skill in the art would appreciate that any sequencing kit or sequencing method capable of solid phase sequencing is contemplated for use. The AutoLoad Solid Phase Sequencing Kit is designed for the direct sequencing of PCR products on the ALF™ family of automated DNA sequences from Amersham Pharmacia Biotech. The Amersham Pharmacia sequencing comb efficiently captures PCR products up to 800 base-pairs in length for use as single-stranded sequencing templates. The sequencing comb enhances sample throughput by eliminating the tedious pipetting normally required when manually loading sequencing gels. The optimized mixtures of ultrapure deoxy- and dideoxynucleotides contain 7-deaza dGTP ($c^7dGTP$) in place of dGTP to minimize problems associated with band compressions and resolutions of heterozygous positions.

C. Components for the Sequencing Reactions:

Reagents: Components Reagent Kit

| A Mix | |
|---|---|
| ddATP | 11.9 µM |
| dATP | 2.38 mM |
| dCTP | 2.38 mM |
| c7dGTP | 1.0 mM |
| dTTP | 2.38 mM |
| Tris-HCl, pH 7.6 | 95.2 mM |
| NaCl | 119 mM |
| C Mix | |
| ddCTP | 11.9 µM |
| dATP | 2.38 mM |
| dCTP | 2.38 mM |
| c7dGTP | 1.0 mM |
| dTTP | 2.38 mM |
| Tris-HCl, pH 7.6 | 95.2 mM |
| NaCl | 119 mM |
| G Mix | |
| ddGTP | 5.0 µM |
| dATP | 2.38 mM |
| dCTP | 2.38 mM |
| c7dGTP | 1.0 mM |
| dTTP | 2.38 mM |
| Tris-HCl, pH 7.6 | 95.2 mM |
| NaCl | 119 mM |
| T Mix | |
| ddTTP | 11.9 µM |
| dATP | 2.38 mM |
| dCTP | 2.38 mM |
| c7dGTP | 1.0 mM |
| dTTP | 2.38 mM |
| Tris-HCl, pH 7.6 | 95.2 mM |
| NaCl | 119 mM |

T7 DNA Polymerase: 8 units/µl in 25 mM Tris-HCl (pH 7.5), 0.25 M NaCl, 5 mMDTT and 50% glycerol Enzyme Dilution Buffer: 20 mM Tris-HCl (pH 7.5), 5 mMDTT, 100 µg/ml BSA and 5% glycerol Annealing Buffer: 1M Tris-HCl (pH 7.5), and 100 mMMgCl$_2$ Extension Buffer: 304 mM citric acid (pH 7.5), 324 mMDTT and 40 mMMnCl$_2$ (pH 7.5)

DMSO: Dimethyl Sulfoxide

Stop Solution: 100% deionized formamide and Dextran Blue 2000 (5 mg/ml)

Sequencing Combs: 8-tooth streptavidin-coated sequencing combs (50 pieces)

10-Well Plates: 10-well plates for PCT product capture, denaturation and annealing steps (30 pieces)

40-Well Plates: 40-well plates for sequencing reactions (10 pieces)

For best results, removal of the stock T7DNA polymerase from storage at −20° C. is minimized except for momentarily to remove an aliquot. During use, all other reagents are kept on ice until required.

TABLE 1

First Round PCR Amplification Primers:

| Primer | Primer Sequence 5' to 3' | Exon | Bases from Exon | Position | Amplicon Length |
|---|---|---|---|---|---|
| 5'AI-1 | SCG CTC TGY GGG GAG AAG CAA | 2–3 | 105 | 26–26 (I1) | 938 |
| 5'BI-1 | GAG GAG MRA GGG GAC CGC AG | 2–3 | 92 | 38–58 (I1) | 940 |
| 5'CI-1 | CGA GGK GCC CGC CCG GCG A | 2–3 | 87 | 44–61 (I1) | 911 |
| 3'AI-3 | GGG AGA YCT AYA GGC GAT CAG G | 2–3 | 46 | 26–57 (I3) | 938 |
| 3'BI-3 | AGS CCA TCC CCG SCG ACC TAT | 2–3 | 56 | 38–58 (I3) | 940 |
| 3'BCI-3 | AGA TCC GGA AGG CTC CCC ACT | 2–3 | 32 | 12–33 (I3) | 911 |

TABLE 1-continued

Second Round PCR Amplification Primers:

| Primer | | Primer sequence 5' to 3' | | | | | | Exon | Sense or Antisense | Bases from Exon | Position | Amplicon Length |
|---|---|---|---|---|---|---|---|---|---|---|---|---|
| 5'I1E2A | G | CGC | CKG | GAS | GAG | GGT | C | 2 | Sense | 47 | 84–100 (I1) | 351 |
| 5'I1E2B | G | CGC | CGG | GAG | GAG | GGT | C | 2 | Sense | 47 | 84–100 (I1) | 351 |
| 5'I1E2C | T | CGG | GCG | GGT | CTC | AGC | C | 2 | Sense | 32 | 99–115 (I1) | 336 |
| 3'I2E2ABC | G | TCS | TGA | CCT | SCG | CCC | C | 2 | Antisense | 34 | 18–34 (I2) | 351 |
| 3'I2E2ABC | G | TCS | TGA | CCT | SCG | CCC | C | 2 | Antisense | 34 | 18–34 (I2) | 351 |
| 3'I2E2ABC | G | TCS | TGA | CCT | SCG | CCC | C | 2 | Antisense | 34 | 18–34 (I2) | 336 |
| 5'I2E3A | G | GGG | GAC | YGG | GCT | GAC | C | 3 | Sense | 33 | 234–251 (I2) | 355 |
| 5'I2E3B | A | CKG | GGC | TGA | CCG | CGG | G | 3 | Sense | 28 | 240–256 (I2) | 360 |
| 5'I2E3C | T | GAC | CRC | GGG | GGC | GGG | G | 3 | Sense | 21 | 247–263 (I2) | 329 |
| 3'AI-3 | G | GGA | GAY | CTA | RAG | GCG | ATC | AGG | 3 | Antisense | 46 | 25–57 (I3) | 355 |
| 3'BI-3 | A | GSC | CAT | CCC | CGS | CGA | CCT | AT | 3 | Antisense | 56 | 38–58 (I3) | 360 |
| 3'BCI-3 | A | GAT | GGG | GAA | GGC | TCC | CCA | CT | 3 | Antisense | 32 | 12–33 (I3) | 329 |

D. Overview of DNA Sequencing Methodology

Although one method of sequencing is hereinbelow provided, one of ordinary skill in the art would appreciate that any method of sequencing could be chosen—i.e. cycle sequencing with TAQ polymerase—yet within the scope contemplated by the present invention. The AutoLoad Solid Phase Sequencing Kit is designed for the direct sequencing of PCR products on the ALF family of automated DNA Sequencers from Pharmacia Biotech. Sequencing is performed using one M13 universal primer tailed primer and one biotinylated primer. The PCR product is captured on a specially designed sequencing comb containing immobilized streptavidin, and the non-biotinylated strand of the PCR product is removed by alkaline denaturation. The immobilized single-stranded product which remains bound to the sequencing comb is then used as a template in dideoxy sequencing reactions using a fluorescently labelled M13 universal primer. The products of the sequencing reaction remain bound to the immobilized template strand until the comb is loaded on the sequencing gel. The wells of the sequencing gel are filled with stop solution, which releases the fluorescently labelled sequencing fragments from the combs. The combs are removed from the sequencing gel and the sequence is started through the computer using a sequence analysis algorithm, one of which could be used is ALF Manager™.

The secondary PCR amplicons (exon 2 and exon 3) may also be sequenced without being bound to a solid support structure—i.e. sequencing may take place in solution or in any other manner compatible with sequencing.

We use the AutoLoad Solid Phase Sequencing Kit to sequence 10 PCR products simultaneously. The Kit provides sufficient combs, reaction plates and reagents to sequence 100 PCR products using T7 DNA Polymerase. One 8-tooth sequencing comb is capable of capturing two templates; four teeth are required per template. The sequencing comb efficiently captures our PCR products of 350 base-pairs and works best with 0.5 mm sequencing gels. The specially designed sequencing combs eliminate the tedious pipetting required when manually loading sequencing gels.

E. Immobilization of the Biotinylated PCR Product

This example describes the simultaneous sequencing of 10 PCR products using the AutoLoad Solid Phase Sequencing Kit. It should be noted, however, that many solid supports would suffice for immobilizing the nested PCR products. Using the AutoLoad Solid Phase Sequencing Kit, a total of five, 8-tooth sequencing combs are required for 10 PCR templates. The sequencing combs can be attached together via the plastic pegs located on each comb and processed as a single unit. The reagent volumes stated in the following instructions are the volumes required to sequence 10 templates. The number of sequencing combs and some reagent volumes must be adjusted if sequencing fewer than 10 templates, one of ordinary skill in the art would be aware of the means to adjust said volumes.

Initially, confirmation must be taken that the PCR product is of the correct size and that the quality and quantity are good (i.e. one sharp band of the expected length and quantity) by agarose electrophoresis. Typically, 40–50 μl of a PCR reaction contains at least 2 pmol of product. This can also be expressed as 1.4 μg/kb PCR product, i.e. to sequence a 350 bp PCR fragment, 700 ng of the product is needed.

Second, addition of 80 μl of 0.5×Binding/Washing buffer (1×binding buffer=2M NaCl+10 mM Tris pH 7.5+1 mM EDTA) to each well of a 10-well plate and then addition of 40–50 μl of PCR reaction mixtures to each of the wells. In order to achieve proper comb orientation when loading sequencing gels the pegs on the sequencing combs should point away from the user when placed on the plate wells.

Third, PCR products are bound to a solid phase support; placing the five, 8-tooth sequencing combs (attached together) in the plate wells and mix gently by moving the combs up and down 2–3 times; incubating the 10-well plate at 65° C. for 30 minutes or at room temperature for at least one hour to ensure complete immobilization of the PCR products on the combs; washing the combs by dipping them in TE buffer in a clean petri dish or allow them to stand for 2 minutes. Immobilization of the PCR product on the sequencing comb is confirmed after incubation by analyzing 4–6 Al of the supernatant from the wells by agarose gel electrophoresis. In this case, the supernatant is simply the solution which remains in the well after the comb is removed.

F. Template Denaturation

Removal of the non-biotinylated strands of the PCR products by alkaline denaturation must be undertaken by placing 120 μl of 0.1 M NaOH solution in each well of a fresh 10-well plate. Place the combs in the wells of the plate and incubate at room temperature for 5 minutes. Remove the combs from the plate and wash the combs by dipping them first in 0.1 M NaOH followed by washes with TE and sterile water.

G. Primer Annealing

The Cy5™-labelled M13 sequencing primer is used in all DNA sequencing reactions. Add the following to each well of a fresh 10-well plate: (1) Annealing buffer—12 μl; (2) Labelled primer—4 μl (4 pmol); and (3) Sterile water—104 μl. Place the file sequencing combs containing the immobilized DNA in the wells of the plate. Heat the plate to 65° C. for 5–10 minutes. Allow the plate to cool at room temperature for 1–10 minutes before proceeding.

H. Sequencing Reactions

Using cold Enzyme Dilution Buffer, dilute the T7 DNA Polymerase to a concentration of 6–8 units/µl. Forty µl of diluted polymerase is required when sequencing 10 templates. Dilute only enough of the stock of T7 DNA Polymerase for immediate use. The diluted polymerase may be stored at 40° C. for up to one week. Mix by gentle pipetting and keep on ice until needed. For maximum stability, do not remove the stock of T7 DNA Polymerase from storage at −20° C. except momentarily to remove an aliquot for dilution.

In order to minimize the pipetting steps required to fill the 40-well plates used for the sequencing reactions, it is necessary to prepare four master mixes, one for each of the four nucleotides. The instructions given for mixtures in Table 2 provide sufficient master mix for the sequencing of 10 PCR templates (one full sequencing gel).

TABLE 2

| Reagent | Volume |
| --- | --- |
| Nucleotide Mix (A, C, G or T) | 30 µl |
| Annealing Buffer | 20 µl |
| Extension Buffer | 10 µl |
| Sterile Water | 190 µl |
| Diluted T7DNA Polymerase | 10 µl |
| DMSO | 20 µl |

Dispense 19 µl of the A "master mix" to each of the 10 "A" wells of a fresh 40-well sequencing reaction plate. Repeat for the other three nucleotide master mixes, placing 19 µl of each mix in the appropriate wells (in the order: A, C, G, T). Prewarm the plate to 37° for 1 minute. Add the combs to the plate, mix (make sure that no air bubbles are trapped in the wells) and incubate at 37° C. for 5 minutes. Place the plate on ice until ready to load on the sequencer.

I. Loading on the ALF DNA Sequencer

Prepare a 6% polyacrylamide gel. Set the water temperature for the thermo plate to 55° C. using the control panel of ALF Manager waiting at least 15 minutes after the gel has reached the set temperature, which is confirmed using ALF Manager, before inserting the sequencing combs in the ALF gel. Add 10 µl of Stop solution to each well of the sequencing gel using a multi-dispensing pipette. Add the same volume of Stop solution to each well for optimal performance. Separate the combs and wash them in the upper buffer reservoir of the sequencer. Place the sequencing combs in the wells, being careful not to push too much of the Stop solution out of the wells. Push the combs down to within approximately 1 mm of the bottom of the gel-wells. Let stand for 10 minutes. Carefully remove the combs, close the lid, set the ALFred thermoplate at 55° C. and start software sequencing.

Loading samples via a combination of pipette and sequencing combs on the same gel can cause lane wandering due to salt concentration differences between the two sample types. For this reason, it is important to specifically commit the DNA sequencers to class I typing as described in this example solely.

In this manner, the HLA-A, -B, or -C alleles can be specifically typed by means of sequence based typing of exons 2 and 3. After receiving sequences for exons 2 and 3, the sequences are combined and compared to an HLA sequence database in order to obtain allele typing.

EXAMPLE 2

We first obtained cells for category two typing. The cells we received required HLA-A, -B, and -C nucleotide sequence analysis. After thawing and resuspending the cells in RPMI 1640 supplemented with 15% fetal calf serum, 10 U/ml penicillin, 10 mg/ml streptomycin, and 2 mM L-glutamine, the cells were counted and cell viability was determined using trypan exclusion. Each sample contained approximately $5 \times 10^6$ total cells, however, viability varied significantly between the three samples. A summary of the cells received and their work-up is shown in Table 3.

TABLE 3

| Pre-Test Sample # | Category | # of Cells Received | Viability | Alleles Sequenced |
| --- | --- | --- | --- | --- |
| 0121-3981-2 | HLA-A | $5 \times 10^6$ | <10% | N.D. |
| 0121-2817-9 | HLA-B | $5 \times 10^6$ | <10% | N.D. |
| 0121-5337-5 | HLA-C | $5 \times 10^6$ | >90% | Cw*0802, *02022 |
| 0104-8698-3 | 2a; HLA-A | $5 \times 10^6$ | >90% | N.D. |
| 0104-9545-5 | 2b; HLA-B | $5 \times 10^6$ | >90% | B*1510, *5001 |

As can be seen from Table 3, samples 3981-2 and 2817-9 were not viable.

Sample 0121-5337-5 was sequenced according to the method hereinabove described and it was determined that Cw*0802 and Cw*02022 were the HLA-C alleles encoded by sample 5337-5. As HLA-B locus is the most polymorphic of the classical HLA class I loci and it is for the HLA-B locus where molecular class I typing techniques have struggled the most, we proceeded typing samples 8698-3 and 9545-5. We sequenced the HLA-B alleles from sample 0104-9545-5 and determined the HLA-B type of this cell line to be B*1510, B*5001.

EXAMPLE 3

Samples 1548 through 1579 (as shown in Table 4) were received as frozen transformed lymphocytes excepting samples 1551, 1552 and 1553 which were delivered as granulocytes. Once these samples were assigned their respective run numbers processing began. DNA extraction using the QIAMP 96 Spin Blood kit was carried out yielding sufficiently good quality DNA at a suitable concentration for primary PCR amplification. 25 µl primary PCR reactions were set up and were checked by loading 5 µl of the amplicon on a 2% agarose gel run at 200 volts for twenty minutes.

Once it was established that the primary PCR had produced a suitable product this was then diluted 1:200 with distilled water ready for the secondary PCR reactions. Each dilution was then used in the four secondary PCR reactions with the resulting amplicons again being checked on a 2% agarose gel. The secondary PCR products then underwent solid phase sequencing reactions using the Amersham Pharmacia Autoload SPS kit and the samples were then loaded onto 6% Page Plus gel and run on a Pharmacia Alfexpress automated DNA sequencer.

The data produced was then analyzed using the Pharmacia HLA Sequityper software (version 2.0) by two independent operators with the results being compared. The HLA type was thereafter reported.

TABLE 4

| NMDP # | Run # | HLA Type |
| --- | --- | --- |
| 506-927-512-4 | 1548 | CW*0701, 0701 |
| 524-926-495-3 | 1549 | CW*0401, 0602 |
| 508-926-702-2 | 1550 | CW*0401, 0401 |

TABLE 4-continued

| NMDP # | Run # | HLA Type |
|---|---|---|
| 524-927-299-8 | 1551 | CW*0304, 0501 |
| 025-0057-0571-0 | 1552 | CW*0602, 0701 |
| 539-926-509-1 | 1553 | CW*1601, 1601 |
| 087-0093-3019-2 | 1554 | CW*0303, 1601 |
| 583-931-288-5 | 1555 | CW*0102, 0501 |
| 045-0075-2598-3 | 1556 | CW*0602, 0701 |
| 087-0092-5150-5 | 1557 | CW*0304, 0702 |
| 030-0161-1687-3 | 1558 | CW*02022, 0702 |
| 592-932-151-4 | 1559 | CW*0702, 0802 |
| 506-922-242-3 | 1560 | CW*0304, 0701 |
| 557-924-917-8 | 1561 | CW*02024, 1701/02 |
| 030-0075-9305-6 | 1562 | CW*0304, 1601 |
| 060-0076-8680-1 | 1563 | CW*0303, 0304 |
| 087-0093-9732-4 | 1564 | CW*0702, 1601 |
| 501-932-447-6 | 1565 | CW*0701, 0802 |
| 506-907-189-5 | 1566 | CW*02022, 0304 |
| 530-932-412-0 | 1567 | CW*0501, 0702 |
| 024-0089-5886-0 | 1568 | CW*0602, 0701 |
| 060-0080-9292-6 | 1569 | CW*0702, 0702 |
| 590-928-963-8 | 1570 | CW*0401, 0501 |

TABLE 5

| Typings | Number | Discrepancy Rate | Sister Laboratory |
|---|---|---|---|
| HLA-A | 1,452 | 2.95% | Oakland |
| HLA-B | 104 | Not Determined | None |
| HLA-C | 2,776 | 2.84% | Maryland Red Cross |

Thus, it should be apparent that there has been provided in accordance with the present invention a method of typing a sample for its HLA-A, -B, or -C type which satisfies the objectives and advantages set forth above. Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

SEQUENCE LISTING

<160> NUMBER OF SEQ ID NOS: 1

<210> SEQ ID NO 1
<211> LENGTH: 15 base pairs
<212> TYPE: DNA
<213> ORGANISM: Artificial Sequence
<220> FEATURE:
<223> OTHER INFORMATION: completely synthesized

<400> SEQUENCE: 1 gta aaa cga cgg cca                             15

TABLE 4-continued

| NMDP # | Run # | HLA Type |
|---|---|---|
| 087-5002-7421-2 | 1571 | CW*0303, 0602 |
| 063-0033-4666-5 | 1572 | CW*0702, 0702 |
| 087-0141-0955-7 | 1573 | CW*0304, 1602 |
| 530-932-168-8 | 1574 | CW*0602, 0704 |
| 533-932-432-8 | 1575 | CW*0501, 0702 |
| 501-932-620-8 | 1576 | CW*0702, 0802 |
| 039-0157-1178-1 | 1577 | CW*0304, 0501 |
| 506-928-758-2 | 1578 | CW*0401, 0701 |
| 524-931-139-0 | 1579 | CW*0303, 0602 |

EXAMPLE 4

As shown in Table 5, during the year of 1997, the invention was used to complete the typing of 1,452 HLA-A, 104 HLA-B, and 2,7776 HLA-C samples. All HLA-C typings were done in duplicate by the American Red Cross in Maryland and all HLA-A typings were duplicated at Oakland Childrens Hospital. Both the Oakland and Maryland facilities are accredited HLA typing laboratories performing PCR-SSOP. Our discrepancy rate with these laboratories was less than 3%, demonstrating a high concordance with other laboratories and typing methodologies in this field using the invention as described herein.

What is claimed is:

1. A method for typing HLA class I alleles, comprising the steps of:

amplifying HLA-A, -B, or -C alleles so as to provide a primary amplicon, wherein the primary amplicon comprises amplified exons 2 and 3 of the HLA-A, -B, or -C alleles in a locus specific manner;

producing at least two secondary HLA-A, -B, or -C locus specific amplicons corresponding to each of the exons 2 and 3 of the primary amplicon, wherein the at least two secondary amplicons are produced by amplifying the primary amplicon by means of using the primary amplicon as a template and nested polymerase chain reaction primers, thereby independently framing each of exon 2 and exon 3 with nested primers in the neighboring introns;

preparing the at least two secondary amplicons for sequencing, wherein the at least two secondary amplicons are provided with an anchoring moiety attached to a first terminus of each of the at least two secondary amplicons and a sequencing primer site attached to a second terminus of each of the at least two secondary amplicons;

attaching the anchoring moiety of each of the at least two secondary amplicons to solid supports; and DNA sequencing each of the at least two secondary amplicons.

2. The method of claim 1, wherein the method further comprises the step of analyzing the DNA sequence of the at least two secondary amplicons so as to provide an HLA class type for the at least two secondary amplicons.

3. The method of claim 1, wherein in the step of preparing the at least two secondary amplicons, the anchoring moiety comprises a biotin molecule.

4. A method for determining tissue compatibility, comprising the steps of:

obtaining a sample of tissue, wherein the sample of tissue contains an amount of HLA-A, -B, or -C alleles;

amplifying the HLA-A, -B, or -C alleles so as to provide a primary amplicon, wherein the primary amplicon comprises amplified exons 2 and 3 of the HLA-A, -B, or -C alleles in a locus specific manner;

producing at least two secondary HLA-A, -B, or -C locus specific amplicons corresponding to each of the exons 2 and 3 of the primary amplicons, wherein the at least two secondary amplicons are produced by amplifying the primary amplicon by means of using the primary amplicon as a template and nested polymerase chain reaction primers located in the introns bordering exons 2 and 3, thereby independently framing each of exon 2 and exon 3;

preparing the at least two secondary amplicons for sequencing, wherein the at least two secondary amplicons are provided with an anchoring moiety attached to a first terminus of each of the at least two secondary amplicons and a sequencing primer site attached to a second terminus of each of the at least two secondary amplicons;

attaching the anchoring moiety of each of the at least two secondary amplicons to solid supports;

DNA sequencing each of the at least two secondary amplicons; and comparing the DNA sequence of the at least two secondary amplicons with at least one predetermined tissue sample.

* * * * *